United States Patent [19]

Lattimore

[11] Patent Number: 5,616,823
[45] Date of Patent: Apr. 1, 1997

[54] CALIBRATION VERIFICATION DEVICE

[75] Inventor: James Lattimore, Safety Harbor, Fla.

[73] Assignee: Johnson & Johnson Medical, Inc., New Brunswick, N.J.

[21] Appl. No.: 576,773

[22] Filed: Dec. 21, 1995

[51] Int. Cl.$^6$ ..................................................... G01N 21/61
[52] U.S. Cl. ............................................ 73/1.03; 73/1.06
[58] Field of Search ...................... 73/1 G; 250/252.1 A, 250/252.1 R; 356/243

[56] References Cited

U.S. PATENT DOCUMENTS

| | | | |
|---|---|---|---|
| 3,825,756 | 7/1974 | Weiss . | |
| 4,302,206 | 11/1981 | Profeta et al. . | |
| 5,067,492 | 11/1991 | Yelderman et al. | 128/719 |
| 5,206,511 | 4/1993 | Apperson et al. | 250/343 |
| 5,397,541 | 3/1995 | Post | 422/88 |

*Primary Examiner*—Robert Raevis
*Attorney, Agent, or Firm*—Woodcock Washburn Kurtz MacKiewicz & Norris

[57] ABSTRACT

A calibration verification device which eliminates the need for calibration gases to verify the calibration of a capnometer and like devices. The calibration verification device (CVD) provides one or more filters which simulate the infrared absorption of the calibration gases. Each filter comprises a thin film deposition on an infrared transparent substrate, where the thin film deposition has a known infrared absorption characteristic which is designed to match that of the desired calibration gas. Since the filter is not a gas, there is no concern about leakage, and the filter may be used to provide a conceivably infinite number of calibration checks within the predetermined tolerances of the capnometer specifications. The filter is placed in a housing which includes means for accurately positioning the filter in the measurement path of the sensor being calibrated as well as means for protecting the filter from damage. In an illustrative embodiment, a simple push-button mechanism is provided for introducing the filter(s) into the measurement path of the sensor during calibration verification.

5 Claims, 4 Drawing Sheets

CALIBRATION VERIFICATION DEVICE

BACKGROUND OF THE INVENTION

1. Field of the Invention

The present invention relates to a calibration verification device which eliminates the need for calibration gases to verify the calibration of a capnometer and any similar devices for measuring gas concentrations. This is accomplished by simulating the infrared absorption of calibration gases using thin films which are mechanically placed in front of the infrared sensor during calibration.

2. Brief Description of the Prior Art

Capnometers function by passing light of a specific wavelength (typically infrared) through a gas and measuring the amount of light that is absorbed. Typically, capnometers measure the amount of carbon dioxide in a patient's breath for medical diagnostic purposes. For this purpose, conventional capnometers comprise an airway adapter, a sensor and a processor box. The airway adapter is typically a hollow aluminum casting with sapphire windows which is inserted in series with the ventilator plumbing and is used to keep the patient's respiratory gases from coming in contact with the sensor mechanism. However, disposable plastic airway adapters are known, as described in U.S. Pat. No. 5,067,492. The sensor is snapped over the airway adapter windows, and the measurement is made directly on the artificial airway through which the patient is breathing. The sensor contains all the optical components necessary to make the infrared measurement and is connected to the processor box by a cable. The processor box powers the sensor, processes the return signal, and presents the data via an LED display.

In order to ensure accurate measurements, capnometer sensors are typically calibrated by taking measurements of sample gases of known concentration prior to taking on-line measurements. For example, in the system of U.S. Pat. No. 5,206,511, gas compules containing gases of known concentration are used for calibrating the sensors. Unfortunately, such gas compules may leak, which, of course, affects the accuracy of the calibration. Also, using sample gases for calibration is cumbersome since it is necessary to keep track of the sample gases and assure the accuracy of the concentrations of the sample gases.

It is desired to develop a calibration verification device which eliminates the need for sample gases to verify the calibration of a capnometer. It is also desired that such a calibration verification device include a simple mechanism for actuation so that the calibration verification process is simple and short in duration. The present invention has been designed to meet these needs.

SUMMARY OF THE INVENTION

The present invention provides a calibration verification device which meets the above-mentioned needs in the prior art. The calibration verification device of the invention meets such needs by simulating the infrared absorption of the calibration gases using one or more filter media comprising a thin film deposition on an infrared transparent substrate. The filter media are disposed in a housing with similar interface geometry as an airway adaptor to facilitate placement of the filter media between the infrared sensor and detector. The housing also contains a simple mechanical spring-actuated design for selectively placing the filter media between the infrared sensor and detector during calibration verification. Since the filter media is stable or nonvolatile, it may be readily introduced, providing an infinite number of calibration checks without using any sample gases. Also, by placing two thin films with different characteristics in a single housing, it is possible to verify four calibration points by overlapping two thin film filters with different transmittances in order to provide four possible combinations of transmittances.

A preferred embodiment of a calibration verification device for verifying the calibration of an infrared sensor in accordance with the invention thus contains one or more filters comprising a thin film deposition on an infrared transparent substrate, where each filter has a known infrared signature corresponding to that of a gas of a known concentration, a housing for protecting the filter between uses, and means for positioning the filters before the infrared sensor for verification of the calibration of the infrared sensor, preferably, the positioning means is a spring actuated push-button mechanism which is pushed by the operator to selectively place the filter in the measurement path of the infrared sensor during calibration verification. Of course, those skilled in the art will appreciate that selective introduction of the filter media into the measurement path may be easily accomplished using other known methods of filter media introduction or activation. The housing, on the other hand, is preferably in the form of an airway adapter which is adapted to fit in the measurement path during calibration verification. By selectively overlapping the filters, two or more thin film filters may be used to simulate the infrared absorption characteristics of different concentrations of carbon dioxide or any other gas for which a calibration measurement is to be made.

BRIEF DESCRIPTION OF THE DRAWINGS

The objects and advantages of the invention will become more apparent and more readily appreciated from the following detailed description of presently preferred exemplary embodiments of the invention taken in conjunction with the accompanying drawings of which.

DETAILED DESCRIPTION OF PRESENTLY PREFERRED EMBODIMENTS

A calibration verification device with the abovementioned beneficial features in accordance with a presently preferred exemplary embodiment of the invention will be described with reference to FIGS. 1–4. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

The present invention eliminates the need for calibration gases to verify the calibration of a capnometer by instead providing a filter which simulates the infrared absorption of the calibration gases. In a preferred embodiment, the filter comprises a thin film deposition on an infrared transparent substrate. The thin film deposition has a known infrared absorption characteristic which is designed to match that of the desired calibration gas. Since the filter is not a gas, there is no concern about leakage, and the filter may be used to provide a conceivably infinite number of calibration checks within the predetermined tolerances of the capnometer specifications. Preferably, the filter is placed in a housing which includes means for accurately positioning the filter in the measurement path of the sensor being calibrated as well as means for protecting the filter from damage and contamination. In a preferred embodiment, a simple push-button mechanism is provided for introducing the filter to the measurement path of the sensor during calibration verification. A preferred embodiment of such a mechanism in conjunction with the housing is illustrated in FIGS. 1 and 2.

Figure 1:
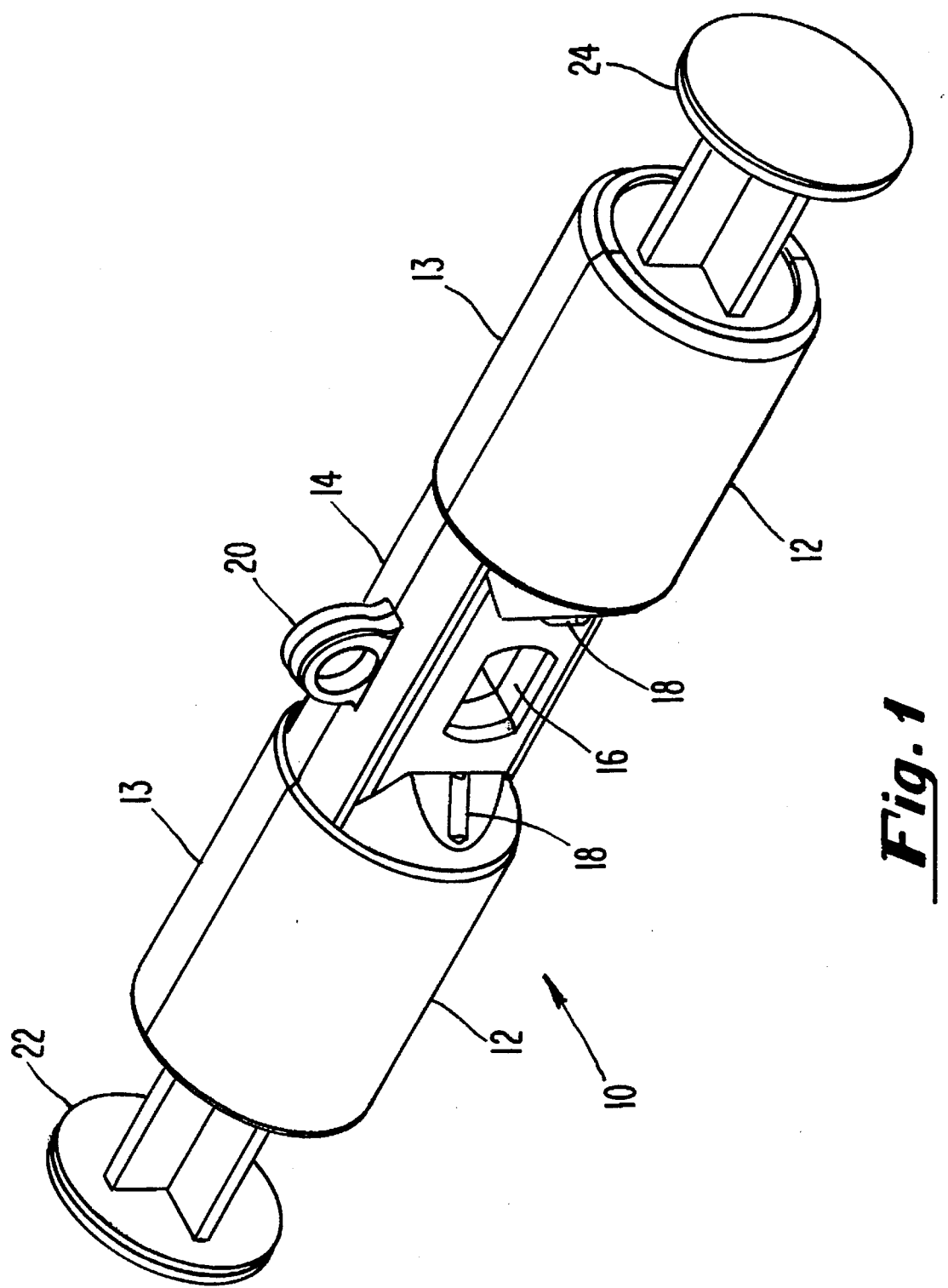
FIG. 1 illustrates a perspective view of a calibration verification device in accordance with a preferred embodiment of the invention.
Figure 2:
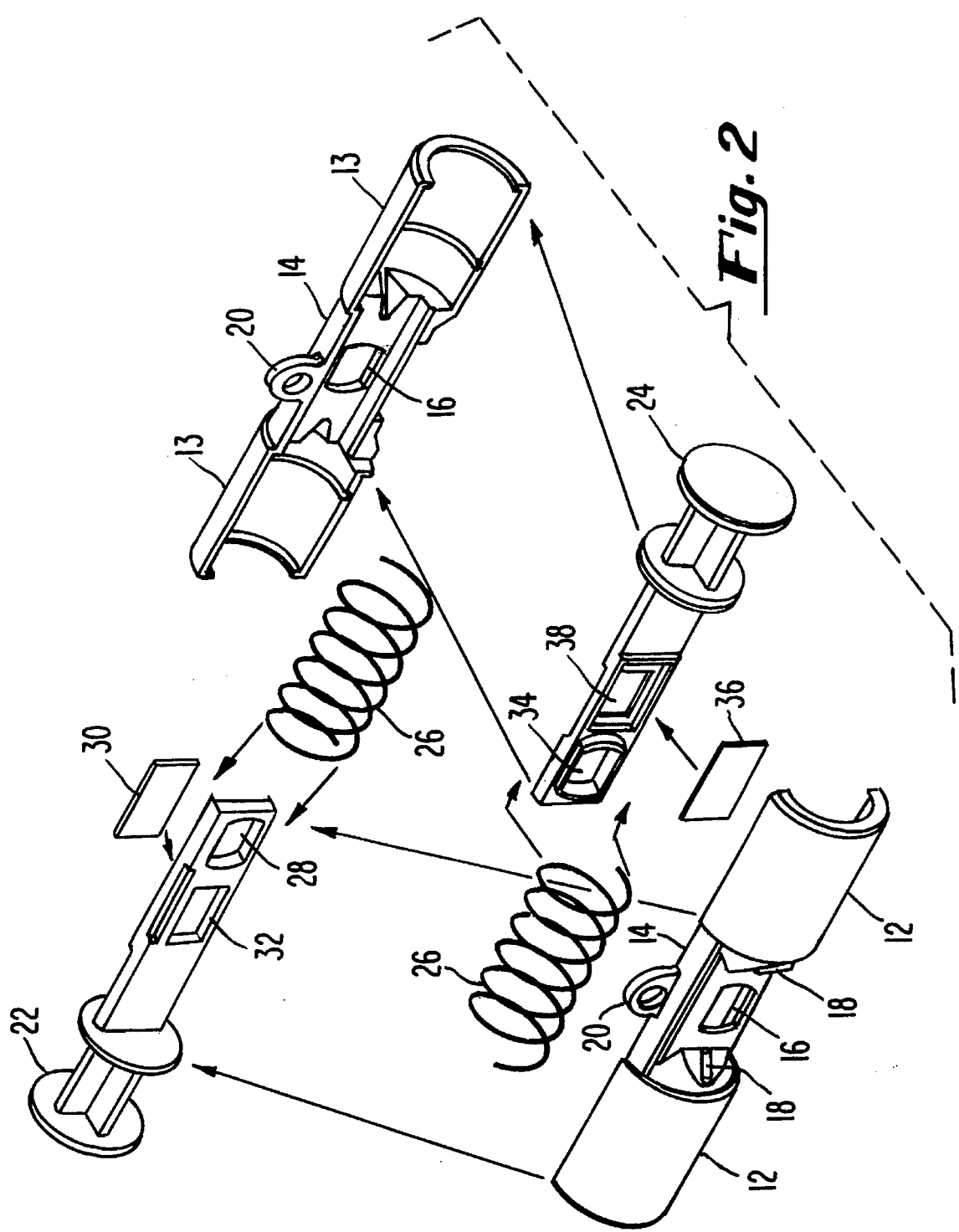
FIG. 2 illustrates an exploded view of the calibration verification device of FIG. 1.
Figure 3:
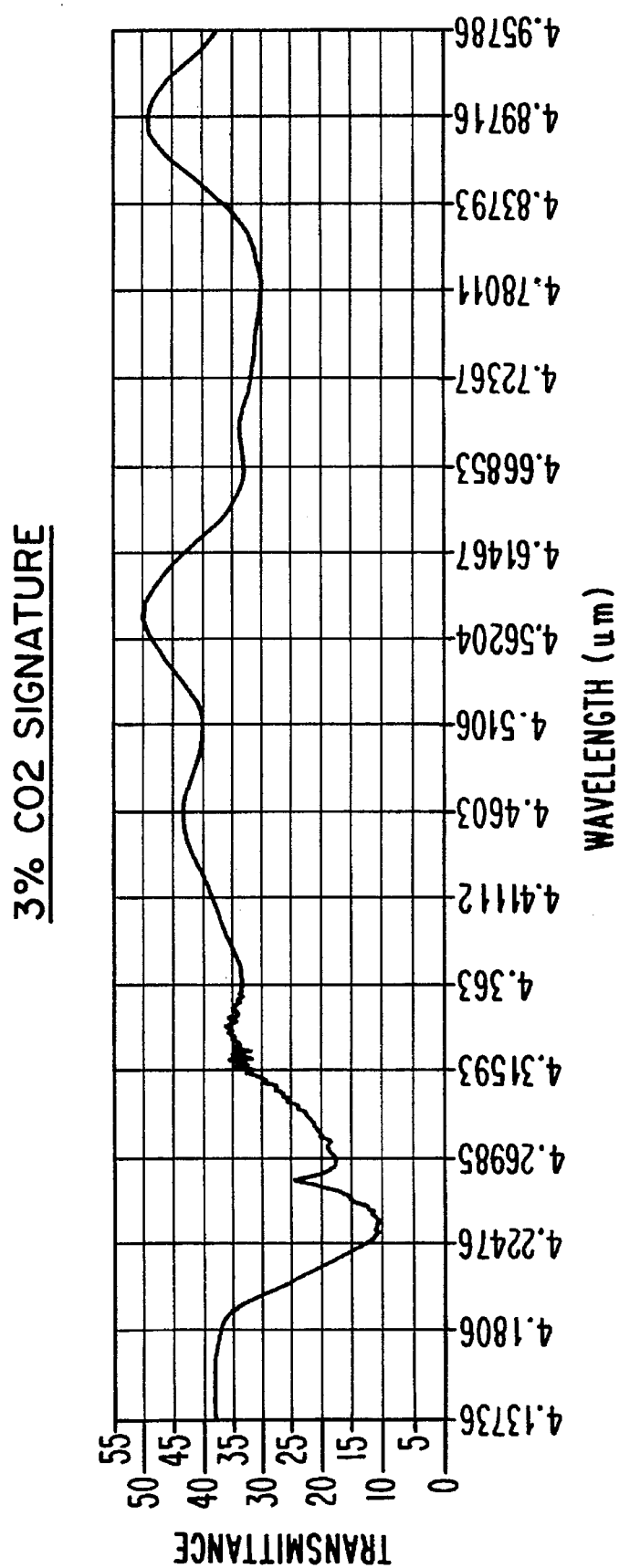
FIG. 3 illustrates a 3% $CO_2$ signature curve in the infrared absorption spectrum which is simulated by a thin film filter for the bandwidth of the target infrared sensor in accordance with the invention.
Figure 4:
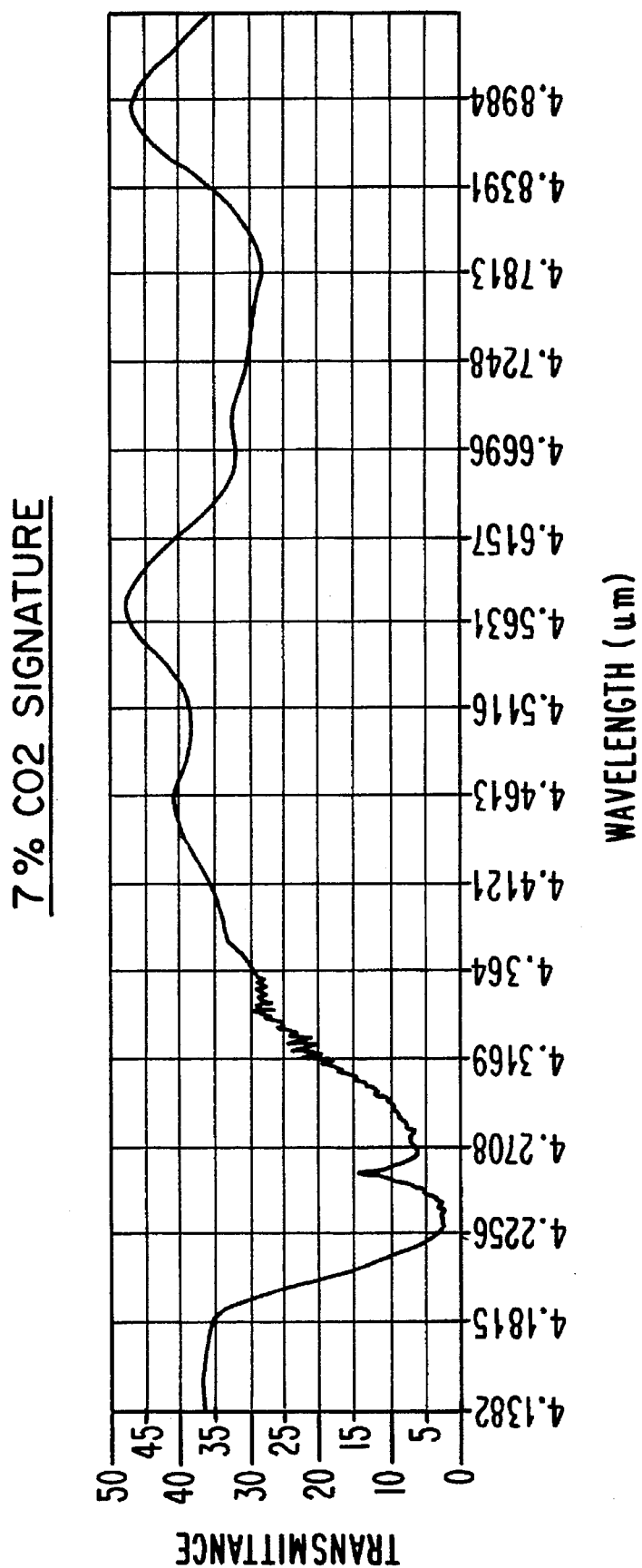
FIG. 4 illustrates a 7% $CO_2$ signature curve in the infrared absorption spectrum which is simulated by a thin film filter for the bandwidth of the target infrared sensor in accordance with the invention.

As shown in FIG. 1, the calibration verification device (CVD) of the invention is preferably formed into the shape of an airway adapter for placement in the measurement path of the capnometer sensor during a calibration verification measurement. As known by those skilled in the art, conventional capnometer sensors make gas concentration measurement through the windows of an airway adapter adapted to fit into the sensor housing so that the windows are in the measurement path of the sensor and allow the measurement circuitry to pass light through the gas sample in the airway adapter for analysis. The airway adapter then connects in series with the tubing used to connect a patient to a mechanical respirator or anesthesia breathing circuit. Hence, to use the CVD of the invention, the airway adapter is snapped out of the housing and the CVD is snapped in for a calibration measurement. After the calibration measurement and/or verification is complete, the CVD is removed and the airway adapter is snapped back in for a gas concentration measurement.

The CVD housing 10 is preferably formed of a hard plastic such as polycarbonate or acetal and is preferably formed in two semi-circular shaped halves 12 and 13 as shown. A center portion 14 is designed to snap fit in place in front of the sensor to be calibrated so that the measurement path of the sensor aligns with window 16 when the protuberances 18 are snap-fit into the sensor's housing (not shown). As shown, CVD 10 may include an anchor 20 in order to facilitate attachment of the CVD to the sensor cable, which assures that the CVD is always readily available for calibration.

In accordance with the invention, the CVD 10 contains actuation extensions 22 and 24 at the respective ends thereof which are biased against springs 26 (FIG. 2) in order to facilitate placement of a calibration filter into the measurement path. As better illustrated in FIG. 2, the extension 22 includes a window 28 which is positioned to coincide with window 16 of the CVD housing 10 when spring 26 is relaxed. A thin film filter 30 in accordance with the invention is preferably placed over opening 32 so that when extension 22 is pressed into the housing 10 against the spring 26, the window 32 containing thin film filter 30 is forced into the measurement path of the sensor against the force of the spring 26. Similarly, the extension 24 includes a window 34 which is positioned to coincide with window 16 of the CVD housing 10 when spring 26 is relaxed. A thin film filter 36 in accordance with the invention is preferably placed over opening 38 so that when extension 24 is pressed into the housing 10 against the spring 26, the window 38 containing thin film filter 36 is forced into the measurement path of the sensor against the force of the spring 26.

The extensions 22 and 24 are preferably provided at opposite ends of the CVD housing 10 and offset with respect to each other so that one or the other or both of the filters 30 and 36 may be placed in the path of the sensor during calibration. In this example, the three possible combinations of filters may represent the infrared spectral signatures of three different concentrations of the same gas, while no filter could indicate a zero reference. Of course, other simple mechanisms may be used to selectively place one or more filters 30, 36 in the sensor's measurement path during calibration, and such mechanisms are left to the discretion of those skilled in the art.

The principal element which makes the present invention possible is the presence of thin film filters 30 and 36. In accordance with the invention, thin film filters 30 and 36 must be selected to have the desired infrared absorption characteristics for the calibration medium. For example, in the case of an infrared capnograph for measuring $CO_2$ concentration in a patient's expired air, a 3% $CO_2$ signature (FIG. 3) and a 7% $CO_2$ signature (FIG. 4) may be used as the sample gases for calibration. In accordance with the invention, respective thin film infrared filters having the illustrated infrared absorption characteristics (signature curves) are selected for use as filters 30 and 36. Of course, other thin film filters would be selected to simulate other gases having different concentrations. Such thin film filters are readily available and may be purchased from vapor deposition specialists, such as OFC Corporation, Natick, Mass. As known to those skilled in the art, such manufacturers prepare thin film filters which simulate as close as possible the spectral response of a designated gas as provided to them. Generally, the manufacturer needs to know the desired wavelength range, the percent reflectance and the percent transmittance for the desired thin film filter. Preferably, the spectral response characteristics provided to the manufacturer also include the effect of the characteristics of the windows of the airway adaptor so that the resulting filter simulates as close as possible the effect of a calibration gas.

Thus, in accordance with the invention, by duplicating the desired infrared spectra of the calibration gases within the bandwidth of the target sensor on a nonvolatile substrate, infrared sensors used for various purposes may be calibrated and/or verified to be within calibration without using sample gases. This results in a more cost effective, easily handled, and reliable calibration and/or verification device than traditionally available.

Although an exemplary embodiment of the invention has been described in detail above, those skilled in the art will readily appreciate that many additional modifications are possible in the exemplary embodiment without materially departing from the novel teachings and advantages of the invention. For example, a plurality of thin film filters may be provided in a single CVD housing 10 in order to facilitate calibration for any of a number of different gases and different concentrations. Accordingly, these and all such modifications are intended to be included within the scope of this invention as defined in the following claims.

What is claimed is:

1. A calibration verification device for verifying the calibration of an infrared sensor for use in gas concentration measurements, comprising:

a filter comprising a thin film deposition on an infrared transparent substrate, said filter having a known infrared signature corresponding to that of a gas of a known concentration;

a filter housing for protecting the filter between uses, said filter housing being formed in the shape of an airway adapter which is adapted to snap-fit into a sensor housing of the infrared sensor; and a push-button mechanism containing said filter and a spring, said push-button mechanism extending out an end of said filter housing and, when pushed against the force of said spring by an operator, selectively places the filter in the measurement path of the infrared sensor for calibration verification.

2. A calibration verification device as in claim 1, further comprising another push-button mechanism containing another spring and another filter, said another filter comprising a thin film deposition on an infrared transparent substrate and having a known infrared signature corresponding to that of a different concentration of said gas besides said known concentration, whereby said another push-button mechanism extends out another end of said filter housing, opposite said end, and is pushed against the force of said another spring by said operator to selectively place said another filter in the measurement path of the infrared sensor for calibration verification.

3. A calibration verification device as in claim 2, wherein said push-button mechanisms are laterally offset with respect to each other so that both said filter and said another filter may be simultaneously placed in the measurement path of said infrared sensor for calibration verification.

4. A calibration verification device as in claim 3, wherein said filter has a known infrared signature corresponding to that of a first concentration of said gas and said another filter has a known infrared signature corresponding to that of a second concentration of said gas, whereby when said filter and said another filter are simultaneously placed in the measurement path of said infrared sensor, the infrared signatures of said filter and said another filter effectively combine to form an infrared signature corresponding to that of a third concentration of said gas.

5. A calibration verification device as in claim 1, wherein said gas is carbon dioxide.

* * * * *